US012582843B2

(12) United States Patent
Shi et al.

(10) Patent No.: US 12,582,843 B2
(45) Date of Patent: Mar. 24, 2026

(54) SYSTEMS AND METHODS FOR DYNAMIC MULTILEAF COLLIMATOR TRACKING

(71) Applicant: SHANGHAI UNITED IMAGING HEALTHCARE CO., LTD., Shanghai (CN)

(72) Inventors: Zhonghua Shi, Shanghai (CN); Wei Zhang, Shanghai (CN); Can Liao, Shanghai (CN); Cheng Ni, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 331 days.

(21) Appl. No.: 18/169,901

(22) Filed: Feb. 16, 2023

(65) Prior Publication Data

US 2023/0191159 A1 Jun. 22, 2023

Related U.S. Application Data

(63) Continuation of application No. PCT/CN2020/110580, filed on Aug. 21, 2020.

(51) Int. Cl.
*A61N 5/10* (2006.01)

(52) U.S. Cl.
CPC .................................. *A61N 5/1047* (2013.01)

(58) Field of Classification Search
None
See application file for complete search history.

(56) References Cited

U.S. PATENT DOCUMENTS

| | | | |
|---|---|---|---|
| 10,625,100 B2 | 4/2020 | Berbeco et al. | |
| 2010/0054409 A1* | 3/2010 | Bose .................... | A61N 5/1049 |
| | | | 378/65 |
| 2010/0252754 A1 | 10/2010 | Brown et al. | |
| 2012/0207370 A1 | 8/2012 | Fahimian et al. | |
| 2013/0142310 A1 | 6/2013 | Fahimian et al. | |
| 2015/0124930 A1 | 5/2015 | Verhaegen et al. | |
| 2017/0128750 A1* | 5/2017 | Filiberti ............... | A61N 5/1069 |

(Continued)

FOREIGN PATENT DOCUMENTS

| | | |
|---|---|---|
| CN | 102397080 A | 4/2012 |
| WO | 2019056134 A1 | 3/2019 |

OTHER PUBLICATIONS

Wu, Hao et al., Comparison of the Positioning Accuracy in MLC Quality Assurance using Various Detectors, Chinese Journal of Medical Physics, 27(4): 1960-1963, 2010.

(Continued)

*Primary Examiner* — Hoon K Song
(74) *Attorney, Agent, or Firm* — METIS IP LLC

(57) ABSTRACT

The present disclosure provides systems and methods for dynamic multileaf collimator (MLC) tracking. A method may include identifying a plurality of working leaves of the MLC at a control point; determining, for the control point, a signal acquisition region of an electronic portal imaging device (EPID) based on a plurality of planned position trajectories of the plurality of working leaves, wherein the signal acquisition region is part of an imaging plane of the EPID and includes a plurality of acquisition rows; and obtaining an image from the EPID at the control point, wherein the image includes information acquired in the signal acquisition region.

20 Claims, 10 Drawing Sheets

(56)                           References Cited

U.S. PATENT DOCUMENTS

| | | |
|---|---|---|
| 2018/0144842 A1 | 5/2018 | Han et al. |
| 2018/0185672 A1 | 7/2018 | Ramezanzadeh Moghadam |
| 2019/0336793 A1 | 11/2019 | Zhou et al. |
| 2020/0061390 A1 | 2/2020 | Ma et al. |
| 2020/0185119 A1 | 6/2020 | Stahl et al. |
| 2022/0032087 A1* | 2/2022 | Cox .................... A61N 5/1045 |

OTHER PUBLICATIONS

International Search Report in PCT/CN2020/110580 mailed on Apr. 12, 2021, 4 pages.
Written Opinion in PCT/CN2020/110580 mailed on Apr. 12, 2021, 5 pages.

* cited by examiner

300

500

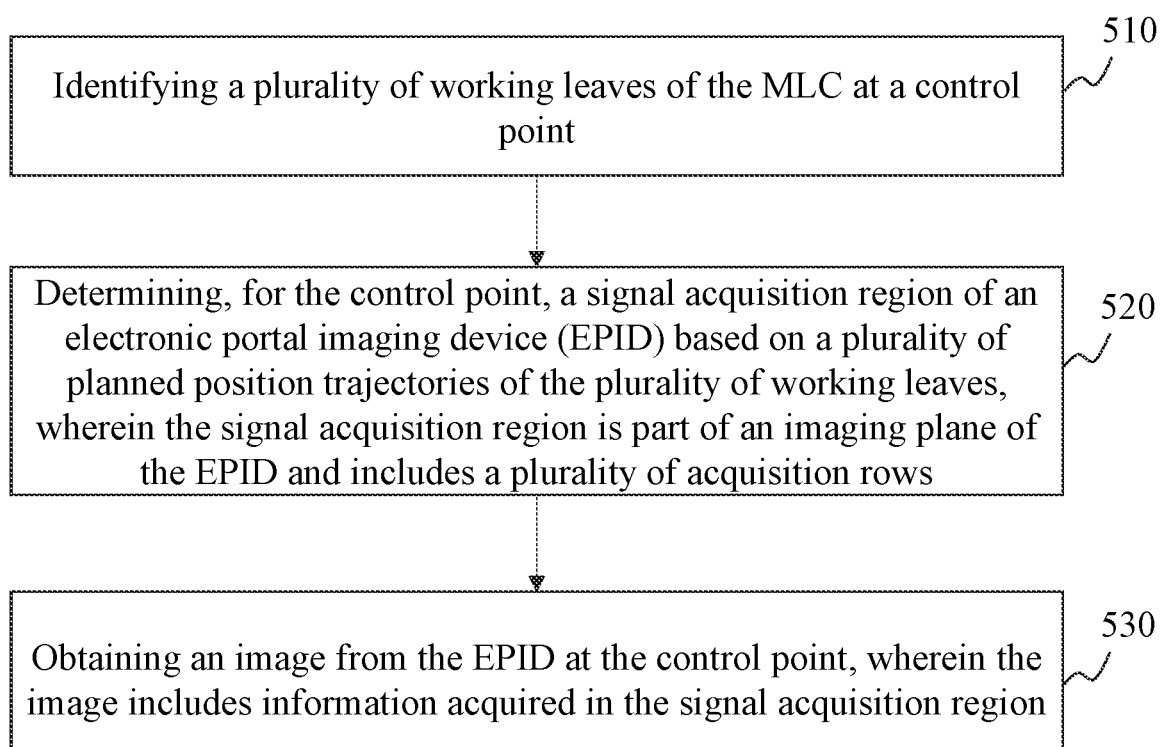

Identifying a plurality of working leaves of the MLC at a control point

510

Determining, for the control point, a signal acquisition region of an electronic portal imaging device (EPID) based on a plurality of planned position trajectories of the plurality of working leaves, wherein the signal acquisition region is part of an imaging plane of the EPID and includes a plurality of acquisition rows

520

Obtaining an image from the EPID at the control point, wherein the image includes information acquired in the signal acquisition region

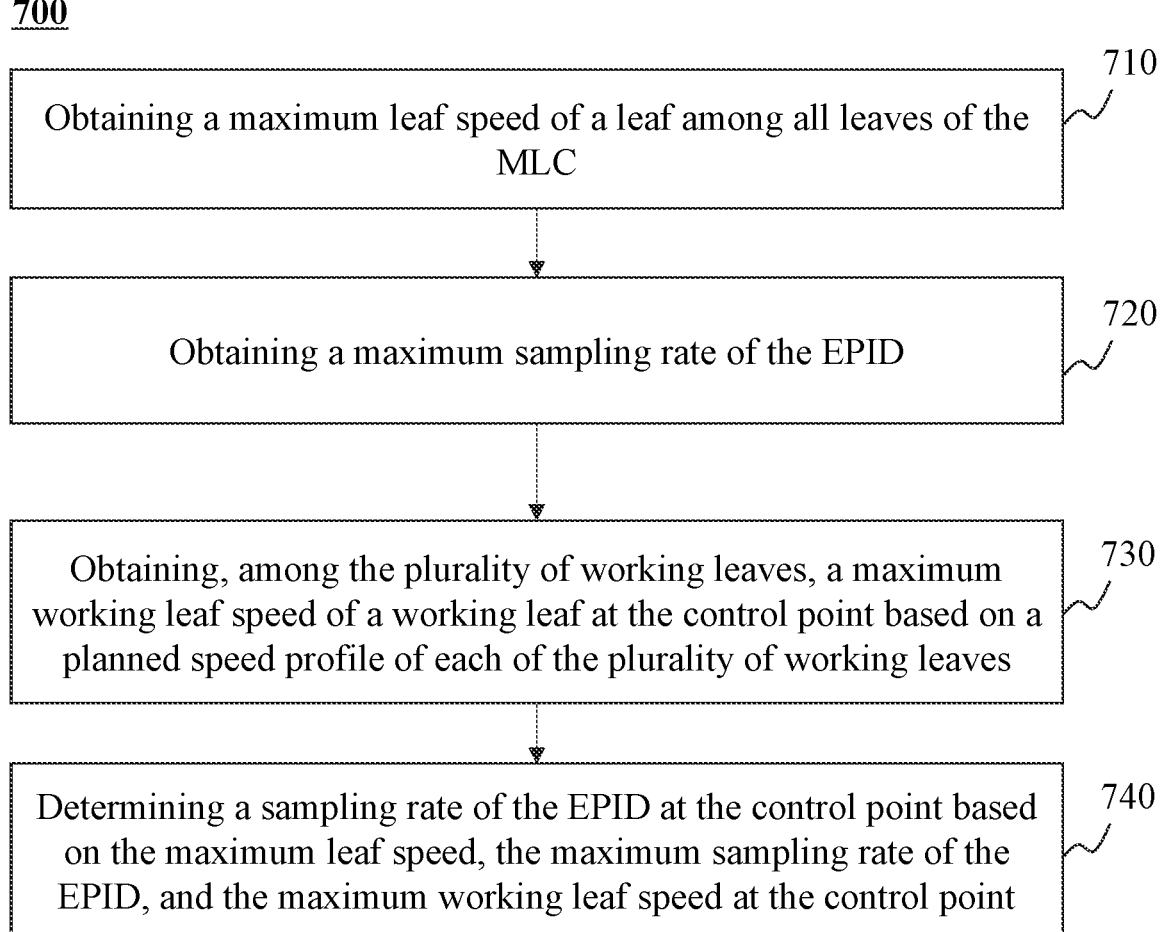

710

Obtaining a maximum leaf speed of a leaf among all leaves of the MLC

720

Obtaining a maximum sampling rate of the EPID

730

Obtaining, among the plurality of working leaves, a maximum working leaf speed of a working leaf at the control point based on a planned speed profile of each of the plurality of working leaves

740

Determining a sampling rate of the EPID at the control point based on the maximum leaf speed, the maximum sampling rate of the EPID, and the maximum working leaf speed at the control point

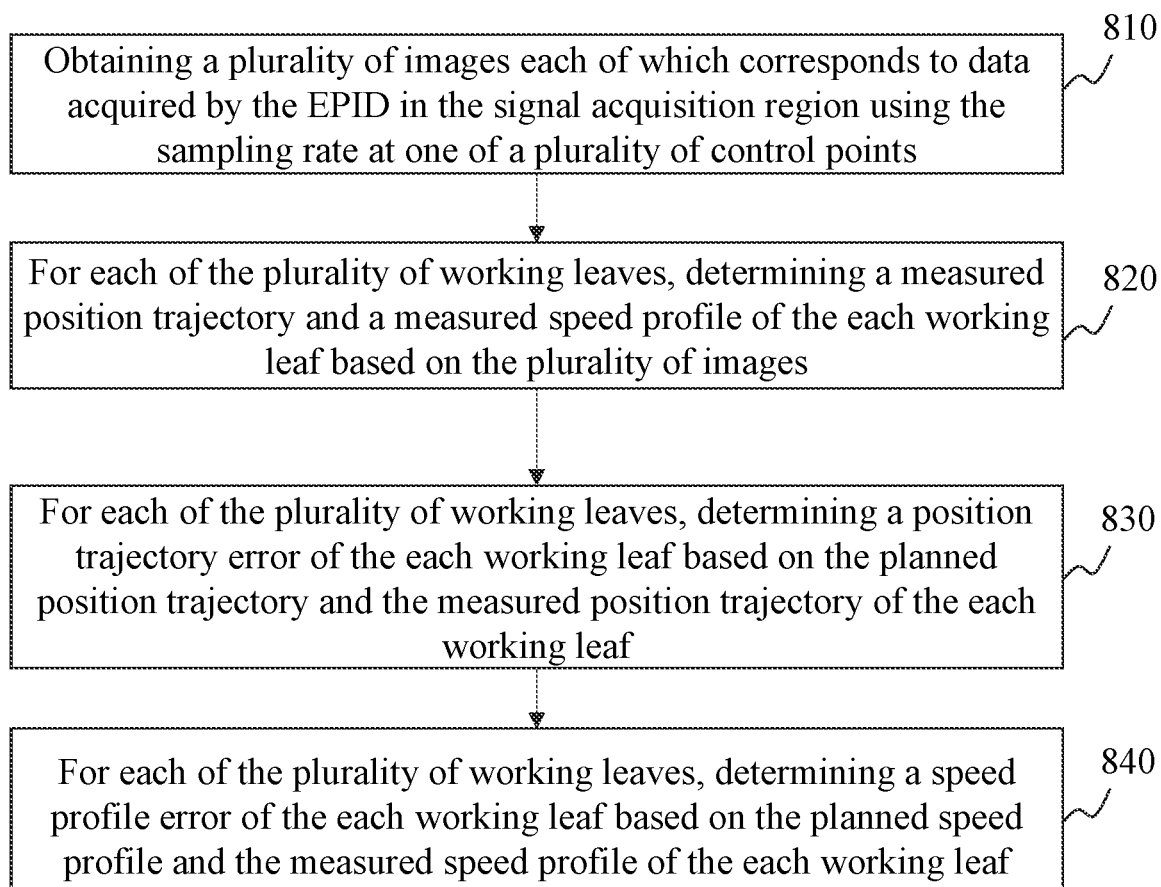

810

Obtaining a plurality of images each of which corresponds to data acquired by the EPID in the signal acquisition region using the sampling rate at one of a plurality of control points

820

For each of the plurality of working leaves, determining a measured position trajectory and a measured speed profile of the each working leaf based on the plurality of images

830

For each of the plurality of working leaves, determining a position trajectory error of the each working leaf based on the planned position trajectory and the measured position trajectory of the each working leaf

840

For each of the plurality of working leaves, determining a speed profile error of the each working leaf based on the planned speed profile and the measured speed profile of the each working leaf

FIG. 8

Time/s

Time/s

<u>1100</u>

SYSTEMS AND METHODS FOR DYNAMIC MULTILEAF COLLIMATOR TRACKING

CROSS-REFERENCE TO RELATED APPLICATIONS

This application is a Continuation of International Application No. PCT/CN2020/110580, filed on Aug. 21, 2020, the contents of which are incorporated herein in their entirety by reference.

TECHNICAL FIELD

The present disclosure generally relates to radiation technologies, and more particularly, to systems and methods for dynamic multileaf collimator (MLC) tracking in radiation.

BACKGROUND

Radiation is widely used in imaging and treatment, e.g., cancer treatment and several other health conditions. MLC plays an important role in dynamic conformal radiation therapy. The movement precision of the MLC is desired to ensure the efficacy of the radiation therapy, especially for a stereotactic radiosurgery (SRS), a stereotactic body radiation therapy (SBRT), etc. Thus, it may be desirable to provide systems and methods for dynamic MLC tracking.

SUMMARY

According to an aspect of the present disclosure, a system for dynamic MLC tracking is provided. The system may include at least one storage device storing executable instructions, and at least one processor in communication with the at least one storage device. When executing the executable instructions, the at least one processor may cause the system to perform one or more of the following operations. The operations may include identifying a plurality of working leaves of the MLC at a control point; determining, for the control point, a signal acquisition region of an electronic portal imaging device (EPID) based on a plurality of planned position trajectories of the plurality of working leaves, wherein the signal acquisition region is part of an imaging plane of the EPID and includes a plurality of acquisition rows; and obtaining an image from the EPID at the control point, wherein the image includes information acquired in the signal acquisition region.

In some embodiments, the operations may further include determining a sampling rate of the EPID at the control point based on a planned speed profile of each of the plurality of working leaves, wherein the image is captured by the EPID using the sampling rate at the control point.

In some embodiments, the determining, for a control point, a signal acquisition region of an EPID includes: obtaining leaf information of the plurality of working leaves based on a planned position trajectory of each of the plurality of working leaves; and determining a start acquisition row and an end acquisition row of the plurality of acquisition rows based on the leaf information of the plurality of working leaves and EPID information of the EPID.

In some embodiments, the leaf information of the plurality of working leaves includes information of a start working leaf, information of an end working leaf, position information of a center leaf of the MLC, and a projection width of a leaf projected upon an isocenter plane of the MLC.

In some embodiments, the EPID information of the EPID includes a pixel size of the EPID, an image size of an image captured by the EPID, a source image distance (SID), and an offset value of a center of the EPID with respect to a beam central axis at the control point.

In some embodiments, the determining a sampling rate of the EPID at the control point includes: obtaining a maximum leaf speed of a leaf among all leaves of the MLC; obtaining a maximum sampling rate of the EPID; obtaining, among the plurality of working leaves, a maximum working leaf speed of a working leaf at the control point based on a planned speed profile of each of the plurality of working leaves; and determining the sampling rate of the EPID at the control point based on the maximum leaf speed, the maximum sampling rate of the EPID, and the maximum working leaf speed at the control point.

In some embodiments, the plurality of planned position trajectories of the plurality of working leaves are determined based on a treatment plan.

In some embodiments, the plurality of planned speed profiles of the plurality of working leaves are determined based on a treatment plan.

In some embodiments, the operations may further include: obtaining a plurality of images each of which corresponds to data acquired by the EPID in the signal acquisition region using the sampling rate at one of a plurality of control points; and for each of the plurality of working leaves, determining a measured position trajectory and a measured speed profile of the each working leaf based on the plurality of images; determining a position trajectory error of the each working leaf based on the planned position trajectory and the measured position trajectory of the each working leaf; and determining a speed profile error of the each working leaf based on the planned speed profile and the measured speed profile of the each working leaf.

In some embodiments, the determining a measured position trajectory and a measured speed profile of each of the plurality of working leaves based on the plurality of images includes: obtaining a plurality of corrected images by correcting, based on an image correction algorithm, the plurality of images; and determining the measured position trajectory and the measured speed profile of the each working leaf based on the plurality of corrected images.

In some embodiments, the determining the measured position trajectory and the measured speed profile of the each working leaf based on the plurality of corrected images includes: for each of the plurality of working leaves, obtaining pixel positions with respect to the each working leaf in each of the plurality of corrected images; determining a field position corresponding to each pixel position based on a predetermined mapping relationship between the pixel positions and the field positions; and obtaining the measured position trajectory and the measured speed profile of the each working leaf based on the field position corresponding to each pixel position and a time synchronization signal, wherein the time synchronization signal is configured to synchronize a first measured time of the measured position trajectory with a first planned time of the planned position trajectory, and synchronize a second measured time of the measured speed profile with a second planned time of the planned speed profile.

According to another aspect of the present disclosure, a method for dynamic MLC tracking is provided. The method may include identifying a plurality of working leaves of the MLC at a control point; determining, for the control point, a signal acquisition region of an electronic portal imaging device (EPID) based on a plurality of planned position trajectories of the plurality of working leaves, wherein the signal acquisition region is part of an imaging plane of the EPID and includes a plurality of acquisition rows; and obtaining an image from the EPID at the control point, wherein the image includes information acquired in the signal acquisition region.

According to still another aspect of the present disclosure, a non-transitory readable medium is provided. The non-transitory readable medium may include at least one set of instructions for dynamic MLC) tracking. When executed by at least one processor of an electrical device, the at least one set of instructions directs the at least one processor to perform a method. The method may include identifying a plurality of working leaves of the MLC at a control point; determining, for the control point, a signal acquisition region of an electronic portal imaging device (EPID) based on a plurality of planned position trajectories of the plurality of working leaves, wherein the signal acquisition region is part of an imaging plane of the EPID and includes a plurality of acquisition rows; and obtaining an image from the EPID at the control point, wherein the image includes information acquired in the signal acquisition region.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 5 is a flowchart illustrating an exemplary process for dynamic MLC tracking according to some embodiments of the present disclosure;

FIG. 7 is a flowchart illustrating an exemplary process for determining a sampling rate at a control point according to some embodiments of the present disclosure;

FIG. 8 is a flowchart illustrating an exemplary process for determining a position trajectory error and a speed profile error of each working leaf according to some embodiments of the present disclosure;

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections or assembly of different levels in ascending order. However, the terms may be displaced by another expression if they achieve the same purpose.

Figure 2:
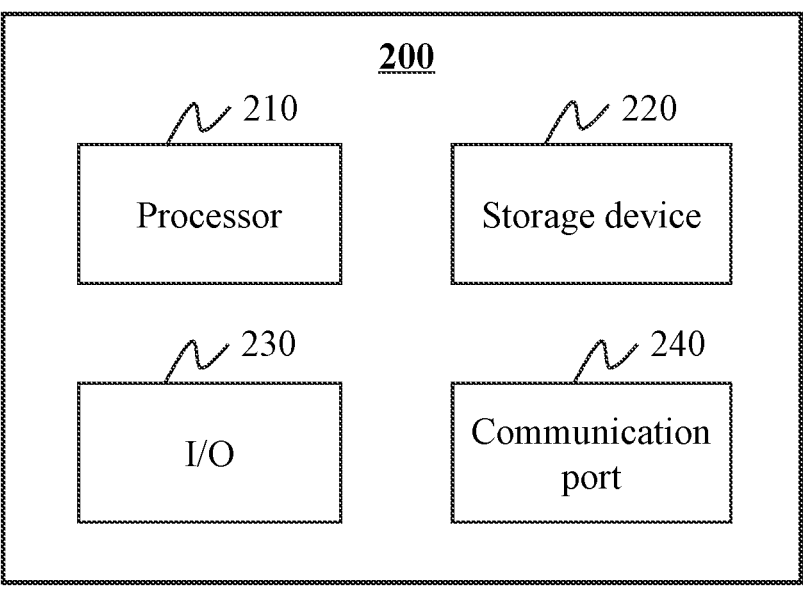
FIG. 2 is a schematic diagram illustrating an exemplary hardware and/or software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

The term "image" in the present disclosure is used to collectively refer to image data (e.g., scan data, projection data) and/or images of various forms, including a two-dimensional (2D) image, a three-dimensional (3D) image, a four-dimensional (4D), etc. The term "pixel" and "voxel" in the present disclosure are used interchangeably to refer to an element of an image. The term "anatomical structure" in the present disclosure may refer to gas (e.g., air), liquid (e.g., water), solid (e.g., stone), cell, tissue, organ of a subject, or any combination thereof, which may be displayed in an image (e.g., a second image, or a first image, etc.) and really exist in or on the subject's body. The term "region," "location," and "area" in the present disclosure may refer to a location of an anatomical structure shown in the image or an actual location of the anatomical structure existing in or on the subject's body, since the image may indicate the actual location of a certain anatomical structure existing in or on the subject's body.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood the operations of the flowcharts may be implemented not in order. Conversely, the operations may be implemented in an inverted order, or simultaneously. Moreover, one or more other operations may be added to the flowcharts. One or more operations may be removed from the flowcharts.

Provided herein are systems and components for non-invasive imaging and/or treatment, such as for disease diagnosis, treatment or research purposes. In some embodiments, the systems may include a radiotherapy (RT) system, a computed tomography (CT) system, an emission computed tomography (ECT) system, an X-ray photography system, a positron emission tomography (PET) system, a magnetic resonance imaging (MRI) system, or the like, or any combination thereof. For illustration purposes, the disclosure describes systems and methods for radiotherapy. The term "image" used in this disclosure may refer to a 2D image, a 3D image, or a 4D image. In some embodiments, the term "image" may refer to an image of a region, e.g., a region of interest (ROI), of a patient. The term "region of interest" or "ROI" used in this disclosure may refer to a part of an image along a line, in two spatial dimensions, in three spatial dimensions, or any of the proceeding as they evolve as a function of time. The image may be an Electronic Portal Imaging Device (EPID) image, a CT image, a fluoroscopy image, an ultrasound image, a PET image, or an MR image. This is not intended to limit the scope of the present disclosure. For persons having ordinary skills in the art, a certain number of variations, changes, and/or modifications may be deduced under the guidance of the present disclosure. Those variations, changes, and/or modifications do not depart from the scope of the present disclosure.

An aspect of the present disclosure relates to systems and methods for dynamic MLC tracking. The systems and methods may use an electronic portal imaging device (EPID) to track positions of leaves of the MLC at a control point during a radiotherapy treatment on or radiation based imaging of a subject. The systems and methods may determine a region (a part of the imaging plane) on an imaging plane of the EPID at the control point. The EPID may only acquire imaging data of the region along a direction parallel to movement directions of the leaves of the MLC, rather than acquiring imaging data of the whole imaging plane. In some embodiments, working leaves may be identified that are used for controlling the shape of the radiation beam at a control point. In some embodiments, a start acquisition row and an end acquisition row of the region may be determined based at least in part on planned position trajectories of the working leaves. In some embodiments, a sampling rate of the EPID at the control point may be determined based on planned speed profiles of the working leaves that are used for controlling the shape of the radiation beams at the control point. By controlling the EPID to acquire the imaging data on the region using the sampling rate at the control point, the amount of imaging data may be reduced and a processing speed may be improved, thereby reducing motion blur effects of the MLC and improving a measurement accuracy of the working leaves during the dynamic MLC tracking.

Figure 1:
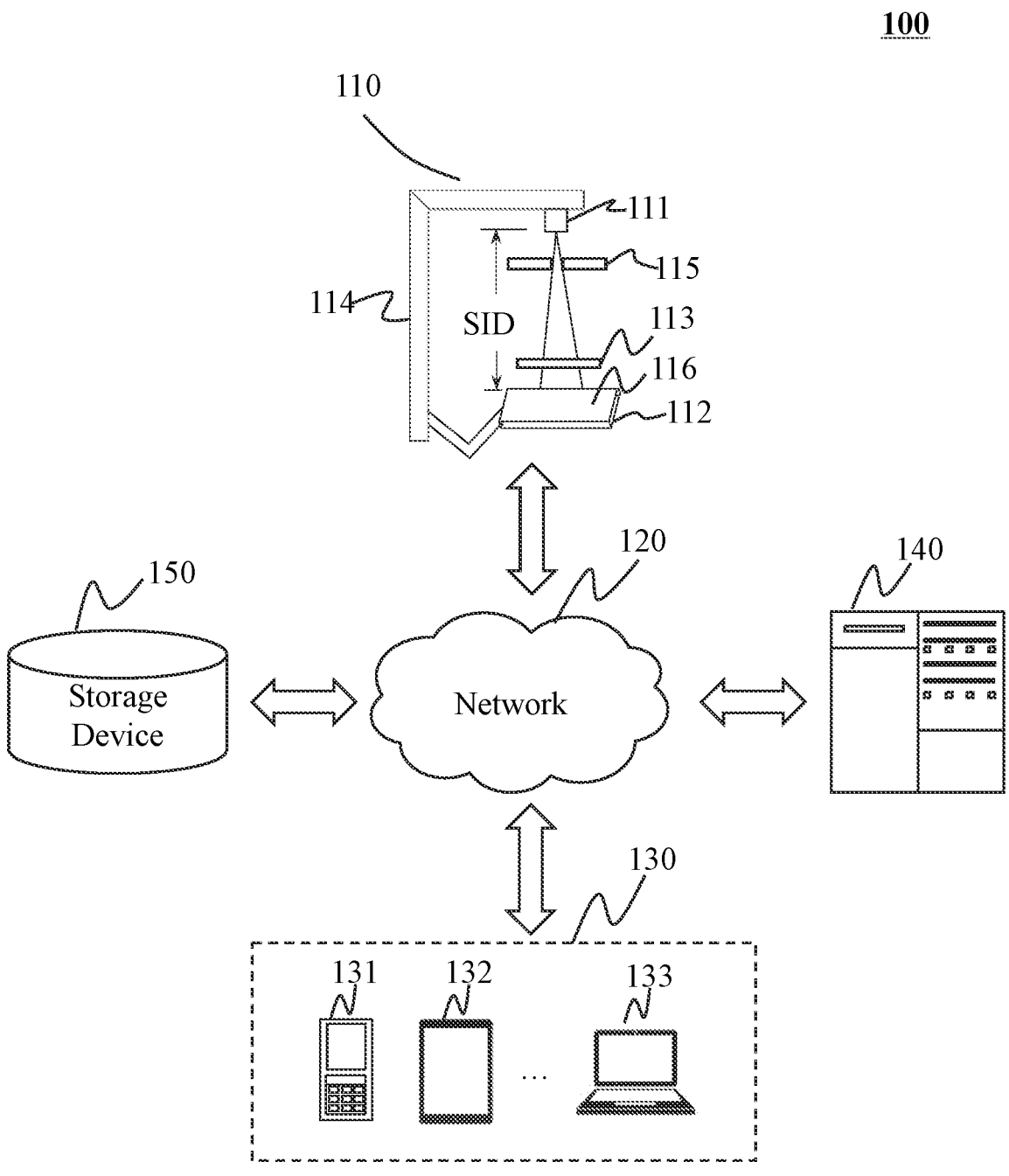
FIG. 1 is a schematic diagram illustrating an exemplary radiotherapy (RT) system according to some embodiments of the present disclosure.

FIG. 1 is a schematic diagram illustrating an exemplary RT system 100 according to some embodiments of the present disclosure. The RT system 100 may include an RT device 110, a network 120, one or more terminals 130, a processing device 140, and a storage device 150. In some embodiments, two or more components of the RT system 100 may be connected to and/or communicate with each other via a wireless connection (e.g., the network 120), a wired connection, or a combination thereof. The connection between the components of the RT system 100 may be variable. Merely by way of example, the RT device 110 may be connected to the processing device 140 through the network 120 or directly. As a further example, the storage device 150 may be connected to the processing device 140 through the network 120 or directly.

The RT device 110 may be configured to deliver a radiotherapy dose to a subject. For example, the RT device 110 may deliver one or more radiation beams to a treatment region (e.g., a tumor) of a subject for causing an alleviation of the subject's symptom. A radiation beam may include a plurality of radiation beamlets. In the present disclosure, "subject" and "object" are used interchangeably. The subject may include any biological subject (e.g., a human being, an animal, a plant, or a portion thereof) and/or a non-biological subject (e.g., a phantom). For example, the subject may include a specific portion of a body, such as the head, the thorax, the abdomen, or the like, or a combination thereof, of the subject. In some embodiments, the RT device 110 may be an image-guided radiation therapy (IGRT) device, a conformal radiation therapy device, an intensity-modulated radiation therapy (IMRT) device, an intensity-modulated arc therapy (IMAT) device, an emission guided radiation therapy (EGRT), a stereotactic radiosurgery (SRS), a stereotactic body radiation therapy (SBRT), or the like.

In some embodiments, the RT device 110 may include a treatment radiation source 111, an electronic portal imaging device (EPID) 112, a couch 113, a gantry 114, and a collimator assembly 115. The treatment radiation source 111 may be configured to emit treatment radiations towards the subject. In some embodiments, the treatment radiation source 111 may be mounted on the gantry 114. The couch 113 may be configured to support the subject to be treated and/or imaged. In some embodiments, the couch 113 may be movable relative to the gantry 114.

The EPID 112 may be configured to acquire an image of the subject and/or the collimator assembly 115. In some embodiments, the EPID 112 may be mounted on the gantry 114 and rotate with the gantry 114. In some embodiments, the EPID 112 may include an imaging plane 116 and a detector (not shown in FIG. 1). In some embodiments, the detector may acquire signals from the whole or part of the imaging plane 116. In some embodiments, the detector may include one or more detector units. The detector unit(s) may include a scintillation detector (e.g., a cesium iodide detector, a gadolinium oxysulfide detector), a solid detector, a liquid ionization chamber, or the like, or any combination thereof. In some embodiments, an imaging radiation source of the EPID may be the treatment radiation source 111.

In some embodiments, the EPID 112 may be at any position associated with the Source Image Distance (SID). For example, the EPID 112 may be at 100 cm SID (i.e., a distance between the treatment radiation source 111 and the imaging plane 116 of the EPID may be 100 cm). In some embodiments, a center of the treatment radiation source 111 and a center of the imaging plane 116 may align. For example, a center of the treatment radiation source 111 and a center of the imaging plane 116 aligning indicates that an offset between the center of the treatment radiation source 111 and the center of the imaging plane 116 is less than a distance threshold (e.g., 1 mm, 2 mm, etc.).

The collimator assembly 115 may be configured to control the shape of the treatment radiations generated by the treatment radiation source 111. In some embodiments, the collimator assembly 115 may include a multi-leaf collimator (MLC) situated in an MLC plane and at least one jaw situated in a jaw plane other than the MLC plane. The MLC may include at least one first group of leaves and at least one second group of leaves opposing each other and being moveable to form an aperture corresponding to a treatment field by blocking pathways of a first portion of the radiation beam within the treatment field. A second portion of the radiation beam may impinge on a radiation target or a portion thereof located in the treatment field. In some embodiments, a gap may exist between the projection of the at least one jaw along a direction of the radiation beam and the treatment field. The at least one jaw may shield or block a part of the first portion of the radiation beam. The MLC and/or the at least one jaw may be made of a radiation-impermeable material. Exemplary radiation-impermeable materials may include tungsten, lead, steel, or the like, or an alloy thereof, or a combination thereof. In some embodiments, a projection of the at least one jaw along the direction of the radiation beam may partially overlap the treatment field, i.e., forming an aperture corresponding to the treatment field together with the MLC.

The network 120 may include any suitable network that can facilitate the exchange of information and/or data for the RT system 100. In some embodiments, one or more components (e.g., the RT device 110, the terminal(s) 130, the processing device 140, the storage device 150, etc.) of the RT system 100 may communicate information and/or data with one or more other components of the RT system 100 via the network 120. For example, the processing device 140 may obtain image data from the RT device 110 (e.g., the EPID 112 of the RT device 110) via the network 120. As another example, the processing device 140 may obtain user (e.g., a doctor, a radiologist) instructions from the terminal(s) 130 via the network 120. The network 120 may be or include a public network (e.g., the Internet), a private network (e.g., a local area network (LAN)), a wired network, a wireless network (e.g., an 802.11 network, a Wi-Fi network), a frame relay network, a virtual private network (VPN), a satellite network, a telephone network, routers, hubs, switches, server computers, and/or any combination thereof. For example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the RT system 100 may be connected to the network 120 to exchange data and/or information.

Figure 3:
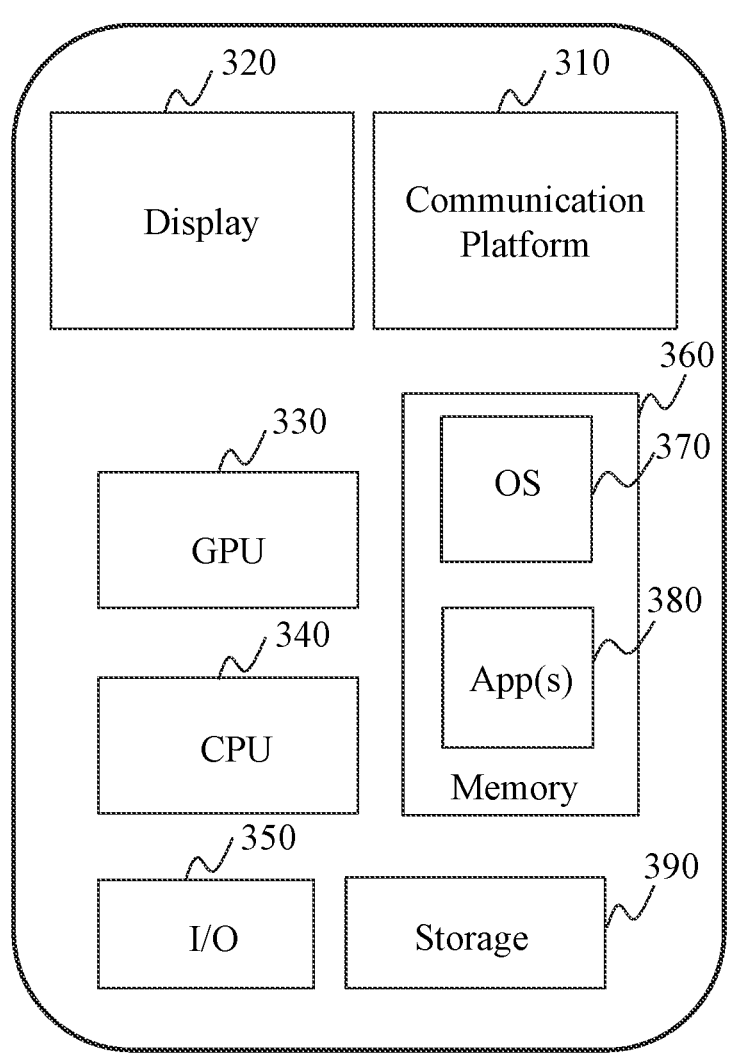
FIG. 3 is a schematic diagram illustrating hardware and/or software components of an exemplary mobile device according to some embodiments of the present disclosure.

The terminal(s) 130 may enable user interaction between a user and the RT system 100. In some embodiments, the terminal(s) 130 may be connected to and/or communicate with the RT device 110, the processing device 140, and/or the storage device 150. For example, the terminal(s) 130 may display a treatment image of the subject obtained from the processing device 140. In some embodiments, the terminal(s) 130 may include a mobile device 131, a tablet computer 132, a laptop computer 133, or the like, or any combination thereof. In some embodiments, the mobile device 131 may include a smart home device, a wearable device, a mobile device, a virtual reality device, an augmented reality device, or the like, or any combination thereof. Merely by way of example, the terminal(s) 130 may include a mobile device as illustrated in FIG. 3. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footwear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 130 may be part of the processing device 140.

The processing device 140 may process information obtained from the RT device 110, the terminal(s) 130, and/or the storage device 150. For example, the processing device 140 may identify a plurality of working leaves of the MLC at a control point and obtain a plurality of planned position trajectories and/or a plurality of planned speed profiles of the plurality of working leaves. The processing device 140 may determine a signal acquisition region (a part of the imaging plane) of the EPID 112 based on the plurality of planned position trajectories for the control point. As another example, the processing device 140 may determine a sampling rate of the EPID 112 at the control point based on the planned speed profiles of the plurality of working leaves. As still another example, the processing device 140 may obtain an image captured by the EPID 112 using the sampling rate at the control point. In some embodiments, the processing device 140 may be a single server or a server group. The server group may be centralized or distributed. In some embodiments, the processing device 140 may be local or remote. For example, the processing device 140 may access information stored in the RT device 110, the terminal(s) 130, and/or the storage device 150 via the network 120. As another example, the processing device 140 may be directly connected to the RT device 110, the terminal(s) 130 and/or the storage device 150 to access stored information. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented by a computing device 200 having one or more components as illustrated in FIG. 2.

The storage device 150 may store data, instructions, and/or any other information. In some embodiments, the storage device 150 may store data obtained from the RT device 110, the terminal(s) 130, and/or the processing device 140. For example, the storage device 150 may store a treatment plan of the subject, an image of the subject and/or the MLC, etc. In some embodiments, the storage device 150 may store data and/or instructions that the processing device 140 may execute or use to perform exemplary methods described in the present disclosure. In some embodiments, the storage device 150 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more other components (e.g., the RT device 110, the processing device 140, the terminal(s) 130) of the RT system 100. One or more components of the RT system 100 may access the data and/or instructions stored in the storage device 150 via the network 120. In some embodiments, the storage device 150 may be directly connected to or communicate with one or more other components (e.g., the RT device 110, the processing device 140, the terminal(s) 130) of the RT system 100. In some embodiments, the storage device 150 may be part of the processing device 140.

It should be noted that the above description regarding the RT system 100 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the RT system 100 may include one or more additional components and/or one or more components of the RT system 100 described above may be omitted. For example, the RT device 110 may further include an imaging component for positioning the radiation target or a portion thereof. The imaging component may include a computed tomography (CT) device (e.g., a cone beam CT (CBCT) device, a fan beam CT (FBCT) device, a multi-slice CT (MSCT) device, etc.), a magnetic resonance imaging (MM) device, an ultrasound imaging device, a fluoroscopy imaging device, a single-photon emission computed tomography (SPECT) device, a positron emission tomography (PET) device, an X-ray imaging device, or the like, or any combination thereof.

FIG. 2 is a schematic diagram illustrating exemplary hardware and/or software components of a computing device 200 according to some embodiments of the present disclosure. The computing device 200 may be used to implement any component of the RT system 100 as described herein. For example, the processing device 140 and/or the terminal(s) 130 may be implemented on the computing device 200, respectively, via its hardware, software program, firmware, or a combination thereof. Although only one such computing device is shown, for convenience, the computer functions relating to the RT system 100 as described herein may be implemented in a distributed fashion on a number of similar platforms, to distribute the processing load. As illustrated in FIG. 2, the computing device 200 may include a processor 210, a storage device 220, an input/output (I/O) 230, and a communication port 240.

The processor 210 may execute computer instructions (e.g., program code) and perform functions of the processing device 140 in accordance with techniques described herein. The computer instructions may include, for example, routines, programs, subjects, components, data structures, procedures, modules, and functions, which perform particular functions described herein. For example, the processor 210 may process image data obtained from the RT device 110, the terminal(s) 130, the storage device 150, and/or any other component of the RT system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method operations that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage device 220 may store data obtained from one or more components of the RT system 100. In some embodiments, the storage device 220 may include a mass storage device, a removable storage device, a volatile read-and-write memory, a read-only memory (ROM), or the like, or any combination thereof. In some embodiments, the storage device 220 may store one or more programs and/or instructions to perform exemplary methods described in the present disclosure. For example, the storage device 220 may store a program to be executed by the processing device 140 to determine signal acquisition regions and sampling rates of the EPID 112. As another example, the storage device 220 may store a program to be executed by the processing device 140 to cause the EPID 112 to capture images based on the signal acquisition regions and sampling rates. As still another example, the processing device 140 may store a program to be executed by the processing device 140 to determine whether the MLC is moved according to a planned speed profile and/or a planned position trajectory.

The I/O 230 may input and/or output signals, data, information, etc. In some embodiments, the I/O 230 may enable a user interaction with the processing device 140. In some embodiments, the I/O 230 may include an input device and an output device. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to another component (e.g., the processing device 140) via, for example, a bus, for further processing. Other types of the input device may include a cursor control device, such as a mouse, a trackball, or cursor direction keys, etc. The output device may include a display (e.g., a liquid crystal display (LCD), a light-emitting diode (LED)-based display, a flat panel display, a curved screen, a television device, a cathode ray tube (CRT), a touch screen), a speaker, a printer, or the like, or a combination thereof.

The communication port 240 may be connected to a network (e.g., the network 120) to facilitate data communications. The communication port 240 may establish connections between the processing device 140 and the RT device 110, the terminal(s) 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee™ link, a mobile network link (e.g., 3G, 4G, 5G), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

FIG. 3 is a schematic diagram illustrating exemplary hardware and/or software components of an exemplary mobile device 300 according to some embodiments of the present disclosure. In some embodiments, one or more terminals 130 and/or a processing device 140 may be implemented on a mobile device 300, respectively.

As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™ Windows Phone™) and one or more applications 380 may be loaded into the memory 360 from the storage 390 in order to be executed by the CPU 340. The applications 380 may include a browser or any other suitable mobile apps for receiving and rendering information relating to the RT system 100. User interactions with the information stream may be achieved via the I/O 350 and provided to the processing device 140 and/or other components of the RT system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
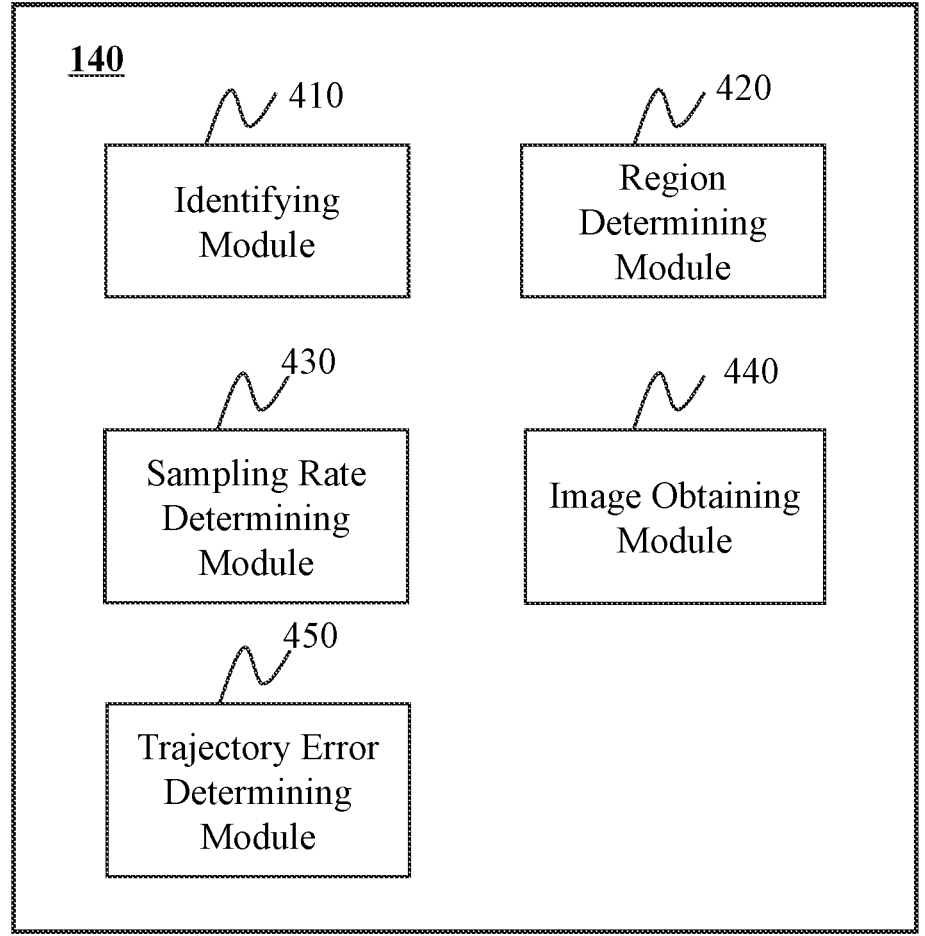
FIG. 4 is a block diagram illustrating an exemplary processing device according to some embodiments of the present disclosure.

FIG. 4 is a block diagram illustrating an exemplary processing device 140 according to some embodiments of the present disclosure. As shown in FIG. 4, the processing device 140 may include an identifying module 410, a region determining module 420, a sampling rate determining module 430, an image obtaining module 440, and a trajectory error determining module 450.

The identifying module 410 may be configured to identify a plurality of working leaves of the MLC at a control point. As used herein, the plurality of working leaves of the MLC at the control point refer to leaves that form an aperture corresponding to a treatment filed at the control point.

The region determining module 420 may be configured to determine a signal acquisition region of the EPID 112. For example, the region determining module 420 may determine, for the control point, the signal acquisition region of the EPID 112 based on a plurality of planned position trajectories of the plurality of working leaves. In some embodiments, the signal acquisition region may be a region on the imaging plane 116 of the EPID 112, from which one or more detectors of the EPID 112 acquire signals. For example, the signal acquisition region may be part of the imaging plane 116 of the EPID 112.

The sampling rate determining module 430 may be configured to determine a sampling rate of the EPID 112. In some embodiments, the sampling rate determining module 430 may determine the sampling rate of the EPID 112 at the control point based on a planned speed profile of each of the plurality of working leaves. For example, the sampling rate determining module 430 may obtain a maximum leaf speed of a leaf among all leaves of the MLC and a maximum sampling rate of the EPID 112. As another example, the sampling rate determining module 430 may obtain, among the plurality of working leaves, a maximum working leaf speed of a working leaf at the control point based on a planned speed profile of each of the plurality of working leaves. As still another example, the sampling rate determining module 430 may determine the sampling rate of the EPID 112 at the control point based on the maximum leaf speed, the maximum sampling rate of the EPID, and the maximum working leaf speed at the control point.

The image obtaining module 440 may be configured to obtain an image from the EPID 112 at the control point. For example, the image obtaining module 440 may obtain the image include information acquired from the signal acquisition region using the sampling rate from the EPID 112

The trajectory error determining module 450 may be configured to determine a position trajectory error and/or a speed profile error of the each working leaf. For example, the trajectory error determining module 450 may determine the position trajectory error of the each working leaf based on a planned position trajectory and a measured position trajectory of the each working leaf. As another example, the trajectory error determining module 450 may determine the speed profile error based on a planned speed profile and a measured speed profile of the each working leaf.

It should be noted that the above descriptions of the processing device 140 are provided for the purposes of illustration, and not intended to limit the scope of the present disclosure. For persons having ordinary skills in the art, various modifications and changes in the forms and details of the application of the above method and system may occur without departing from the principles of the present disclosure. In some embodiments, the processing device 140 may include one or more other modules and/or one or more modules described above may be omitted. For example, the processing device 140 may also include a transmission module configured to transmit signals (e.g., electrical signals, electromagnetic signals) to one or more components (e.g., the RT device 110, the terminal(s) 130, the storage device 150) of the RT system 100. As a further example, the processing device 140 may include a storage module (not shown) used to store information and/or data (e.g., a treatment plan, images, etc.) associated with the dynamic MLC tracking. Additionally or alternatively, two or more modules may be integrated into a single module and/or a module may be divided into two or more units. For example, the region determining module 420 and the sampling rate determining module 430 may be combined as an EPID parameter determining module to determine the signal acquisition regions and sampling rates of the EPID. As another example, the trajectory error determining module 450 may be divided into a position trajectory error determining unit and a speed profile error determining unit to determine the position trajectory error and the speed profile error of a leaf of the MLC, respectively. However, those variations and modifications also fall within the scope of the present disclosure.

FIG. 5 is a flowchart illustrating an exemplary process 500 for dynamic MLC tracking according to some embodiments of the present disclosure. In some embodiments, process 500 may be executed by the RT system 100. For example, the process 500 may be implemented as a set of instructions (e.g., an application) stored in a storage device (e.g., the storage device 150, the storage device 220, and/or the storage 390). In some embodiments, the processing device 140 (e.g., the processor 210 of the computing device 200, the CPU 340 of the mobile device 300, and/or one or more modules illustrated in FIG. 4) may execute the set of instructions and may accordingly be directed to perform the process 500.

In 510, the processing device 140 (e.g., the identifying module 410) may identify a plurality of working leaves of the MLC at a control point.

In some embodiments, during a radiotherapy session of the subject, the RT device 110 (e.g., the treatment radiation source 111, the EPID 112, the gantry 114, the collimator assembly 115) may rotate around the subject using a plurality of rotation angles relative to an axis perpendicular to the couch 113. In some embodiments, each control point may correspond to a rotation angle among the plurality of rotation angles. In some embodiments, each control point may correspond to a treatment field.

In some embodiments, the MLC may include at least one first group of leaves and at least one second group of leaves opposing each other and being moveable to form an aperture corresponding to a treatment field by blocking pathways of a first portion of the radiation beam within the treatment field. A second portion of the radiation beam may impinge on a radiation target (e.g., a subject or a portion thereof) located in the treatment field. In some embodiments, the subject may include a biological subject (e.g., a human, an animal), a non-biological subject (e.g., a phantom), or the like, or a combination thereof. For example, the subject may include a patient. As another example, the subject may include a specific portion, such as the chest, a breast, and/or the abdomen of the patient. In some embodiments, the radiation target may be an anatomical structure. For example, the radiation target may include an organ, tissue, a blood vessel, or the like, or a combination thereof, of the subject.

As used herein, a plurality of working leaves of the MLC at the control point refer to leaves that form the aperture corresponding to the treatment filed at the control point. In some embodiments, before the radiotherapy session is performed on the subject (e.g., days or weeks before the treatment commences), a treatment plan of the subject may be determined. For example, the treatment plan may be determined based on a planned image of the subject captured by an imaging device (e.g., the EPID 112 or an imaging component of the RT device 110). Using the planned image, one or more radiation targets of the subject may be identified and located. In some embodiments, the treatment plan may describe at least one treatment field to be applied to the subject at each of the plurality of control points. For example, the treatment plan may include a planned fraction duration, a planned radiation dose, a planned radiation energy delivery direction, a planned beam shape of a radiation beam, a planned cross-sectional area of the radiation beam at a specific location along the direction that the radiation beam travels, a planned region of interest (ROI) (e.g., the radiation target in the subject), or the like, or any combination thereof.

In some embodiments, the processing device 140 may identify the plurality of working leaves based on the treatment plan. For example, the processing device 140 may identify leaves that form the planned beam shape of the radiation beam as the plurality of working leaves. In some embodiments, the processing device 140 may identify a position (or a sequence number) of each working leaf among the plurality of working leaves. The sequence number and the position of a working leaf may be determined mutually.

In 520, the processing device 140 (e.g., the region determining module 420) may determine, for the control point, a signal acquisition region of the EPID 112 based on a plurality of planned position trajectories of the plurality of working leaves.

In some embodiments, the signal acquisition region may be a region on the imaging plane 116 of the EPID 112, from which one or more detectors of the EPID 112 acquire signals. For example, the signal acquisition region may be part of the imaging plane 116 of the EPID 112. The signal acquisition region may at least include image information of the treatment field shaped by the plurality of working leaves of the MLC. In some embodiments, the one or more detectors may scan data on the imaging plane 116 row by row to acquire the signals for imaging. A direction of the row scanning may be parallel to a moving direction of the working leaves of the MLC. In some embodiments, the signal acquisition region may include a plurality of acquisition rows. The plurality of acquisition rows may include a start acquisition row and an end acquisition row by the scanning time. The start acquisition row may be a first row from which the one or more detectors of the EPID 112 acquire signals. The end acquisition row may be a last row from which the one or more detectors of the EPID 112 acquire signals. For example, the imaging plane 116 may be divided into 20 rows along the direction that is within the plane the leaves of the MLC are arranged and perpendicular to the moving direction of the working leaves. For instance, the leaves of the MLC are arranged in an X-Y plane and working leaves move along the X direction to form an aperture conforming to a treatment field, the imaging plane 116 may be divided into 20 rows along the Y direction. The leaves of the MLC may be numbered from the first to the twentieth. The plurality of acquisition rows may include 10 rows. The start acquisition row may be the fifth row, and the end acquisition row may be the fourteenth row among the 20 rows. The signal acquisition region may be a rectangular region between the fifth row and the fourteenth row, and two borders the imaging plane 116. The two borders may be perpendicular to the scanning direction that is from the first row to the twentieth row of the leaves of the MLC, or vice versa. In some embodiments, each control point may correspond to a signal acquisition region. For example, the processing device 140 may determine a signal acquisition region for each control point.

In some embodiments, each working leaf of the plurality of working leaves may have a planned position trajectory. The planned position trajectory may indicate a planned position of the working leaf at each time point or each control point during the radiotherapy session of the subject. If each working leaf moves to the corresponding planned position at the corresponding time point or the corresponding control point, the plurality of working leaves may form the treatment field of the treatment plan at the control point. In some embodiments, the plurality of planned position trajectories of the plurality of working leaves may be determined based on the treatment plan.

In some embodiments, the processing device 140 may obtain leaf information of the plurality of working leaves based on a planned position trajectory of each of the plurality of working leaves. The leaf information may include information of a start working leaf, information of an end working leaf, information of a center leaf of the MLC, a projection width of a leaf projected upon an isocenter plane of the MLC, or the like, or any combination thereof. In some embodiments, the start acquisition row may be a first row regarding which the one or more detectors of the EPID 112 acquire signals. In some embodiments, the end acquisition row may be a last row regarding which the one or more detectors of the EPID 112 acquire signals. In some embodiments, the information of the start working leaf and/or the end working leaf may include a planned position of the start working leaf and/or the end working leaf, the numbering of the start working leaf and/or the end working leaf, or the like, or any combination thereof. In some embodiments, the information of a center leaf of the MLC may include information regarding a position of the center leaf of the MLC. In some embodiments, the center leaf may be a leaf at the center of the MLC. In some embodiments, the projection width of a leaf projected upon the isocenter plane of the MLC may be a width of the leaf that is projected on the isocenter plane. The isocenter plane may be a plane that passes through an isocenter and is perpendicular to a beam central axis of the treatment radiation source 111. The isocenter plane may be parallel to the imaging plane 116. The beam central axis may be a line passing through a center of the treatment radiation source 111 and a center of a plane formed by the radiation beam emitted from the treatment radiation source 111, which is perpendicular to a propagation direction of the radiation beam. The isocenter may be a point in space where beam central axis of the treatment radiation source 111 intersect when the gantry 114 rotates during the radiotherapy session.

In some embodiments, the processing device 140 may determine the start acquisition row and the end acquisition row of the plurality of acquisition rows (or the signal acquisition region) based on the leaf information of the plurality of working leaves and EPID information of the EPID 112. In some embodiments, the EPID information of the EPID 112 may include a pixel size of the EPID 112, an image size of an image captured by the EPID 112, a source image distance (SID), an offset value of a center of the EPID 112 with respect to a beam central axis at the control point, or the like, or any combination thereof. In some embodiments, the pixel size of the EPID 112 may be a size of a pixel on the imaging plane 116. The pixel size may be calculated by dividing the size of the imaging plane 116 by a predetermined resolution. In some embodiments, the imaging size of the image captured by the EPID 112 may be a size of an image captured by the EPID 112. For example, the imaging size may be equal to a size of the imaging plane 116 of the EPID 112. In some embodiments, the SID may be a distance between the treatment radiation source 111 and the imaging plane 116. For example, the SID may be 100 cm. In some embodiments, the offset value of the center of the EPID 112 with respect to the beam central axis may be a distance between the center of the imaging plane 116 and the beam central axis. In some embodiments, different rotation angles may correspond to different offset values. For example, if the beam central axis of the treatment radiation source 111 is perpendicular to the ground (i.e., the rotation angle is 0), the center of the imaging plane 116 may align with the beam central axis (the center of the imaging plane 116 is on the beam central axis). If the gantry 114 rotates to an angle other than 0, the center of the imaging plane 116 may be away from the beam central axis due to gravity. The distance between the center of the imaging plane 116 and the beam central axis may be the offset value. In some embodiments, the offset values corresponding to different rotation angles may be predetermined and stored in a storage device (e.g., the storage device 150, the storage device 220, the storage 390, etc.).

In some embodiments, the processing device 140 may determine the start acquisition row and the end acquisition row of the signal acquisition region based on the leaf information of the plurality of working leaves and the EPID information. For example, the processing device 140 may determine a start acquisition row an end acquisition row at a control point A according to Equation (1) and Equation (2), respectively:

$$StartRow = \tag{1}$$
$$\frac{[-(CenterLeaf - StartLeaf) * LeafWidth * SID + PanelShift]}{PixelSize} + $$
$$\frac{ImageSize}{2},$$

$$EndRow = \tag{2}$$
$$\frac{[(EndLeaf - CenterLeaf) * LeafWidth * SID + PanelShift]}{PixelSize} + \frac{ImageSize}{2},$$

where StartRow denotes a position of the acquisition row, CenterLeaf denotes a sequence number of a center leaf of the MLC, StartLeaf denotes a sequence number of a start working leaf at the control point A, EndLeaf denotes a sequence number of an end working leaf at the control point A, LeafWidth denotes a projection width of a leaf projected upon an isocenter plane of the MLC at the control point A, SID denotes a source image distance at the control point A, PanelShift denotes an offset value of a center of the EPID 112 with respect to a beam central axis at the control point A, PixelSize denotes a pixel size of the EPID 112, and ImageSize denotes an image size of an image captured by the EPID 112 at the control point A. In some embodiments, the sequence number and the position of a working leaf may be determined mutually.

In 530, the processing device 140 (e.g., the image obtaining module 440) may obtain an image from the EPID 112 at the control point.

Figure 6:
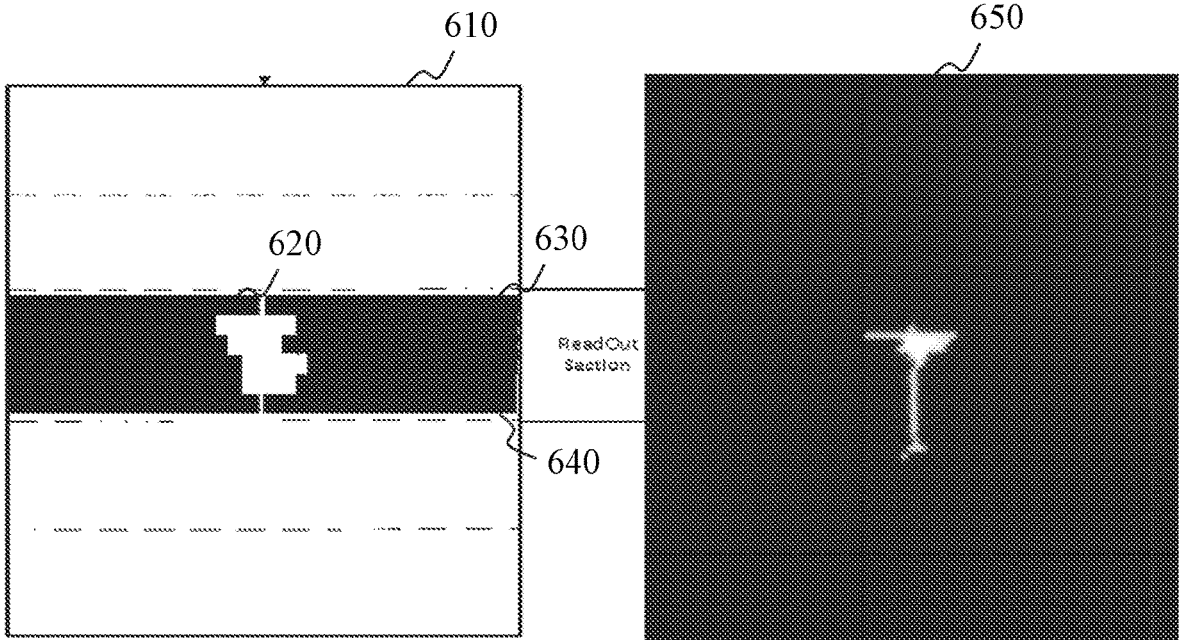
FIG. 6 is a schematic diagram illustrating an exemplary signal acquisition region and an exemplary image according to some embodiments of the present disclosure.

In some embodiments, the image may include information acquired from the signal acquisition region. For example, for the control point, the one or more detectors of the EPID 112 may scan the imaging plane 116 between the start acquisition row and the end acquisition row to acquire the information of the signal acquisition region. FIG. 6 is a schematic diagram illustrating an exemplary signal acquisition region 620 and an exemplary image 650 according to some embodiments of the present disclosure. As shown in FIG. 6, the signal acquisition region 620 may be part of an imaging plane 610. The signal acquisition region 620 may include a start acquisition row 630 and an end acquisition row 640, and the region between the start acquisition row 630 and the end acquisition row 640. The one or more detectors of the EPID 112 may scan the imaging plane 610 between the start acquisition row 630 and the end acquisition row 640, and may obtain the image 650. The remaining regions on the imaging plane 116 except for the signal acquisition region 620 may be assigned with a value (e.g., a gray value of each pixel in the remaining regions) equal to a value of a pixel being shaded by the leaves of the MLC.

In some embodiments, the processing device 140 (e.g., the sampling rate determining module 430) may determine a sampling rate of the EPID 112 at the control point based on a planned speed profile of each of the plurality of working leaves. In some embodiments, the image may be captured by the EPID 112 using the sampling rate at the control point. In some embodiments, each control point may correspond to a sampling rate. The EPID 112 may capture images using different sampling rates at different control points. In some embodiments, the sampling rate at a control point may be determined based on speeds of working leaves at the control point. Since the working leaves are not always moved at high speeds (e.g., no less than 25 mm/s), redundant images may be obtained if the EPID 112 captures images using high sampling rates (e.g., no less than 120 frames/s) all the time, thereby causing unnecessary burden on image processing. In some embodiments, the sampling rate at a control point may be proportional to a maximum speed of a working leaf among the plurality of working leaves at the control point. For example, more images may be captured by the EPID 112 at a control point M than at a control point N, where the maximum speed among the plurality of working leaves at control point M is higher than the maximum speed among the plurality of working leaves at the control point N.

In some embodiments, each working leaf of the plurality of working leaves may have a planned speed profile. The planned speed profile may indicate a planned speed of the working leaf at each time point or each control point during the radiotherapy session of the subject. If each working leaf moves at the corresponding planned speed at the corresponding time point or the corresponding control point, the plurality of working leaves may form the treatment field specified in the treatment plan at the control point. In some embodiments, the plurality of planned speed profiles of the plurality of working leaves may be determined based on the treatment plan. In some embodiments, the processing device 140 may obtain a maximum working leaf speed of a working leaf at the control point from the planned speed profile of each of the plurality of working leaves. In some embodiments, the processing device 140 may obtain the maximum speed of a working leaf among the plurality of working leaves at the control point from the planned speed profile of each of the plurality of working leaves. In some embodiments, an exemplary process for determining a sampling rate at a control point may be found elsewhere (e.g., FIG. 7 and the descriptions thereof) in the present disclosure.

It should be noted that the above description regarding the process 500 is merely provided for the purposes of illustration, and not intended to limit the scope of the present disclosure. For persons having ordinary skills in the art, multiple variations and modifications may be made under the teachings of the present disclosure. In some embodiments, the process 500 may be accomplished with one or more additional operations not described and/or without one or more of the operations discussed above. For example, the processing device 140 may further store the image obtained from the EPID 112 in a storage device (e.g., the storage device 150, the storage device 220, and/or the storage 390). However, those variations and modifications do not depart from the scope of the present disclosure.

FIG. 7 is a flowchart illustrating an exemplary process 700 for determining a sampling rate at a control point according to some embodiments of the present disclosure. In some embodiments, process 700 may be executed by the RT system 100. For example, the process 700 may be implemented as a set of instructions (e.g., an application) stored in a storage device (e.g., the storage device 150, the storage device 220, and/or the storage 390). In some embodiments, the processing device 140 (e.g., the processor 210 of the computing device 200, the CPU 340 of the mobile device 300, and/or one or more modules illustrated in FIG. 4) may execute the set of instructions and may accordingly be directed to perform the process 700.

In 710, the processing device 140 (e.g., the sampling rate determining module 430) may obtain a maximum leaf speed of a leaf among all leaves of the MLC.

In some embodiments, the maximum leaf speed may be a maximum speed at which a leaf, among all leaves of the MLC, can move. The maximum leaf speed may be a predetermined value and stored in a storage device (e.g., the storage device 150, the storage device 220, and/or the storage 390). For example, the maximum leaf speed may be 25 mm/s. In some embodiments, the processing device 140 may access the storage device to obtain the maximum speed.

In 720, the processing device 140 (e.g., the sampling rate determining module 430) may obtain a maximum sampling rate of the EPID 112.

In some embodiments, the maximum sampling rate of the EPID 112 may be a maximum rate that the EPID 112 captures images. The maximum sampling rate may be a predetermined value and stored in a storage device (e.g., the storage device 150, the storage device 220, and/or the storage 390). For example, the maximum sampling rate may be 120 frames/s. In some embodiments, the processing device 140 may access the storage device to obtain the maximum sampling rate.

In 730, the processing device 140 (e.g., the sampling rate determining module 430) may obtain, among the plurality of working leaves, a maximum working leaf speed of a working leaf at the control point based on a planned speed profile of each of the plurality of working leaves.

In some embodiments, the maximum working leaf speed may be a maximum speed of a working leaf among the plurality of working leaves. In some embodiments, the processing device 140 may obtain speeds of the plurality of working leaves from the planned speed profile of each of the plurality of working leaves. The processing device 140 may compare the speeds of the plurality working leaves to identify the maximum working leaf speed of the working leaf at the control point.

In 740, the processing device 140 (e.g., the sampling rate determining module 430) may determine the sampling rate of the EPID 112 at the control point based on the maximum leaf speed, the maximum sampling rate of the EPID, and the maximum working leaf speed at the control point.

In some embodiments, the processing device 140 may determine the sampling rate of the EPID 112 at the control point according to an algorithm based on the maximum leaf speed, the maximum sampling rate of the EPID, and the maximum working leaf speed at the control point. For example, the processing device 140 may determine the sampling rate of the EPID 112 at the control point according to Equation (3):

$$F = \frac{V_{MAX-W}}{V_{MAX}} * F_{MAX}, \qquad (3)$$

where F denotes the sampling rate of the EPID 112 at the control point, $V_{MAX-W}$ denotes the maximum working leaf speed of a working leaf at the control point, $V_{MAX}$ denotes the maximum leaf speed of a leaf among all leaves of the MLC, and $F_{MAX}$ denotes the maximum sampling rate of the EPID 112.

It should be noted that the above description regarding the process 700 is merely provided for the purposes of illustration, and not intended to limit the scope of the present disclosure. For persons having ordinary skills in the art, multiple variations and modifications may be made under the teachings of the present disclosure. In some embodiments, the process 700 may be accomplished with one or more additional operations not described and/or without one or more of the operations discussed above. For example, the processing device 140 may store the sampling rate of the EPID 112 at the control point in a storage device (e.g., the storage device 150, the storage device 220, and/or the storage 390). However, those variations and modifications do not depart from the scope of the present disclosure.

FIG. 8 is a flowchart illustrating an exemplary process 800 for determining a position trajectory error and a speed profile error of each working leaf according to some embodiments of the present disclosure. In some embodiments, process 800 may be executed by the RT system 100. For example, the process 800 may be implemented as a set of instructions (e.g., an application) stored in a storage device (e.g., the storage device 150, the storage device 220, and/or the storage 390). In some embodiments, the processing device 140 (e.g., the processor 210 of the computing device 200, the CPU 340 of the mobile device 300, and/or one or more modules illustrated in FIG. 4) may execute the set of instructions and may accordingly be directed to perform the process 800.

In 810, the processing device 140 (e.g., the trajectory error determining module 450) may obtain a plurality of images each of which corresponds to data acquired by the EPID 112 in the signal acquisition region using the sampling rate at one of a plurality of control points.

In some embodiments, the processing device 140 may identify the plurality of control points during the radiotherapy session of the subject. The EPID 112 may obtain at least one image using the sampling rate at each control point. Each of the at least one image may include data acquired in the signal acquisition region corresponding to the each control point.

In 820, for each of the plurality of working leaves, the processing device 140 (e.g., the trajectory error determining module 450) may determine a measured position trajectory and a measured speed profile of the each working leaf based on the plurality of images.

In some embodiments, the measured position trajectory may indicate a measured position of the each working leaf at each time point or each control point during the radiotherapy session of the subject. In some embodiments, the processing device 140 may synchronize time points of the plurality of images and time points of the RT system 100. For instance, the time point of an image may be recorded as the time the image is acquired by the RT system 100, thereby synchronizing the time points of the plurality of images and the time points of the RT system 100. In some embodiments, after the time synchronization between the plurality of images and the RT system 100, the processing device 140 may correct one or more of the plurality of images with respect to errors caused by, e.g., a geometric offset of the EPID 112, the RT system 100, etc. For example, the processing device 140 may obtain a plurality of corrected images by correcting, based on an image correction algorithm, the plurality of images. The image correction algorithm may include a bad point correction algorithm, a dark field correction algorithm, a gain correction algorithm, a plate offset correction algorithm, a tilt correction algorithm, a SID correction algorithm, or the like, or any combination thereof. In some embodiments, the image correction algorithm may be a correction chart or a correction table. For example, the correction chart or the correction table may include a correction value corresponding to each control point. The processing device 140 may look up the correction chart or a correction table to obtain the corresponding correction value using the corresponding control point. In some embodiments, the image correction algorithm may be predetermined and stored in a storage device (e.g., the storage device 150, the storage device 220, and/or the storage 390).

In some embodiments, the processing device 140 may determine the measured position trajectory and the measured speed profile of the each working leaf based on the plurality of corrected images. In some embodiments, the processing device 140 may identify each working leaf in the plurality of corrected images and obtain a measured position of the each working leaf The processing device 140 may record the measured position of the each working leaf and the corresponding time point to obtain the measured position trajectory of the each working leaf. The processing device 140 may identify a position changes with time from the plurality of corrected images to obtain the measured speed profile of the each working leaf. Exemplary processes for determining the measured position trajectory and the measured speed profile of the each working leaf may be found elsewhere (e.g., FIG. 11 and the descriptions thereof) in the present disclosure.

In 830, for each of the plurality of working leaves, the processing device 140 (e.g., the trajectory error determining module 450) may determine a position trajectory error of the each working leaf based on the planned position trajectory and the measured position trajectory of the each working leaf.

Figure 9:
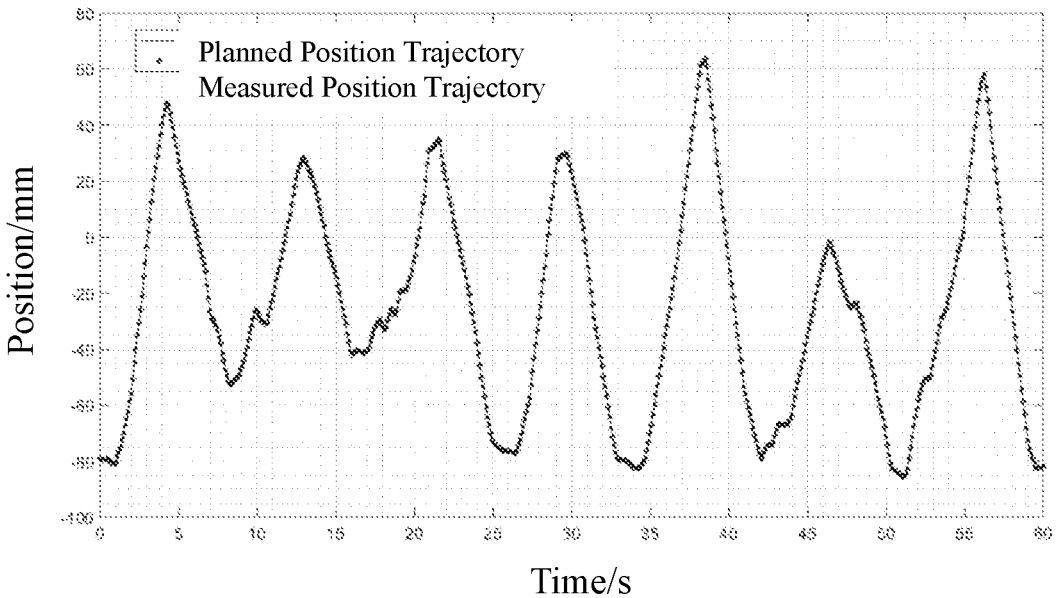
FIG. 9 is a schematic diagram illustrating an exemplary planned position trajectory and an exemplary measured position trajectory of a working leaf according to some embodiments of the present disclosure.
Figure 10:
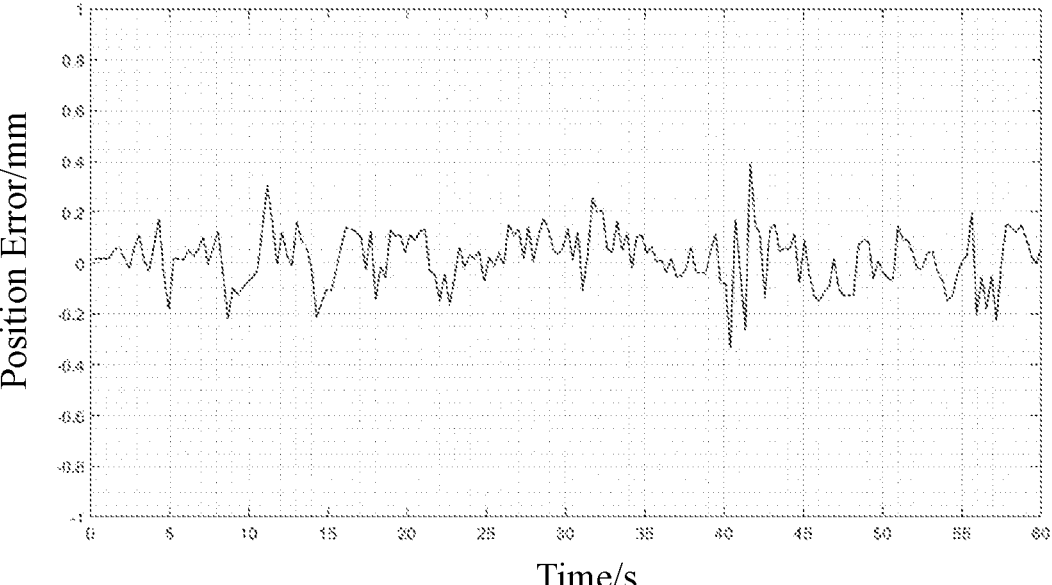
FIG. 10 is a schematic diagram illustrating an exemplary position trajectory error of a working leaf according to some embodiments of the present disclosure.

In some embodiments, the position trajectory error of a working leaf may indicate a difference between a measured position and a planned position of each working leaf at each time point or each control point. In some embodiments, the processing device 140 may compare the planned position trajectory and the measured position trajectory of a same working leaf to obtain a position trajectory error of the same working leaf. FIG. 9 is a schematic diagram illustrating an exemplary planned position trajectory and an exemplary measured position trajectory of a working leaf according to some embodiments of the present disclosure. FIG. 10 is a schematic diagram illustrating an exemplary position trajectory error of a working leaf according to some embodiments of the present disclosure. As shown in FIG. 9, the planned position trajectory of the working leaf is presented as a smooth line, and the measured position trajectory of the working leaf is presented as a dotted line. The measured position trajectory and the planned position trajectory may be compared, and a difference between the planned position trajectory and the measured position trajectory may be designated as the position trajectory error as shown in FIG. 10.

In 840, for each of the plurality of working leaves, the processing device 140 (e.g., the trajectory error determining module 450) may determine a speed profile error of the each working leaf based on the planned speed profile and the measured speed profile of the each working leaf In some embodiments, the speed profile error of a working leaf may indicate a difference between a measured speed and a planned speed of each working leaf at each time point or each control point. In some embodiments, the processing device 140 may compare the planned speed profile and the measured speed profile of a same working leaf to obtain a speed profile error of the same working leaf.

In some embodiments, the planned position and/or speed of each of one or more working leaves may be determined from the planned position trajectory and/or the planned speed profile, and a time point corresponding to the planned position and/or speed of each of the one or more working leaves according to the treatment plan may be determined. The time point corresponding to the planned position and/or speed may be designated as a first time point of the RT system. The measured position and/or speed of each of one or more working leaves may be determined from the measured position trajectory and/or the measured speed profile, and a time point corresponding to the measured position and/or speed of each of the one or more working leaves may be determined. The time point corresponding to the measured position and/or speed of each of the one or more working leaves may be designated as a second time point of the RT system 100. The first time point of the RT system 100 and the second time point of the RT system 100 may be synchronized. In some embodiments, a planned position and/or speed and a measured position and/or speed of the same working leaf at each time point may be compared to obtain a position error and/or speed error at each time point, thereby obtaining the position trajectory error and/or speed profile error of the working leaf.

In some embodiments, the speed profile error and/or the position trajectory error of the each working leaf may be used for evaluating a dynamic error of the each working leaf during the radiotherapy session of the subject. In some embodiments, the speed profile error and/or the position trajectory error of the each working leaf may be compared with a predetermined threshold to determine whether the each working leaf is moved according to the treatment plan.

It should be noted that the above description regarding the process 800 is merely provided for the purposes of illustration, and not intended to limit the scope of the present disclosure. For persons having ordinary skills in the art, multiple variations and modifications may be made under the teachings of the present disclosure. In some embodiments, the process 800 may be accomplished with one or more additional operations not described and/or without one or more of the operations discussed above. For example, the processing device 140 may store the plurality of images at the plurality of control points in a storage device (e.g., the storage device 150, the storage device 220, and/or the storage 390). However, those variations and modifications do not depart from the scope of the present.

Figure 11:
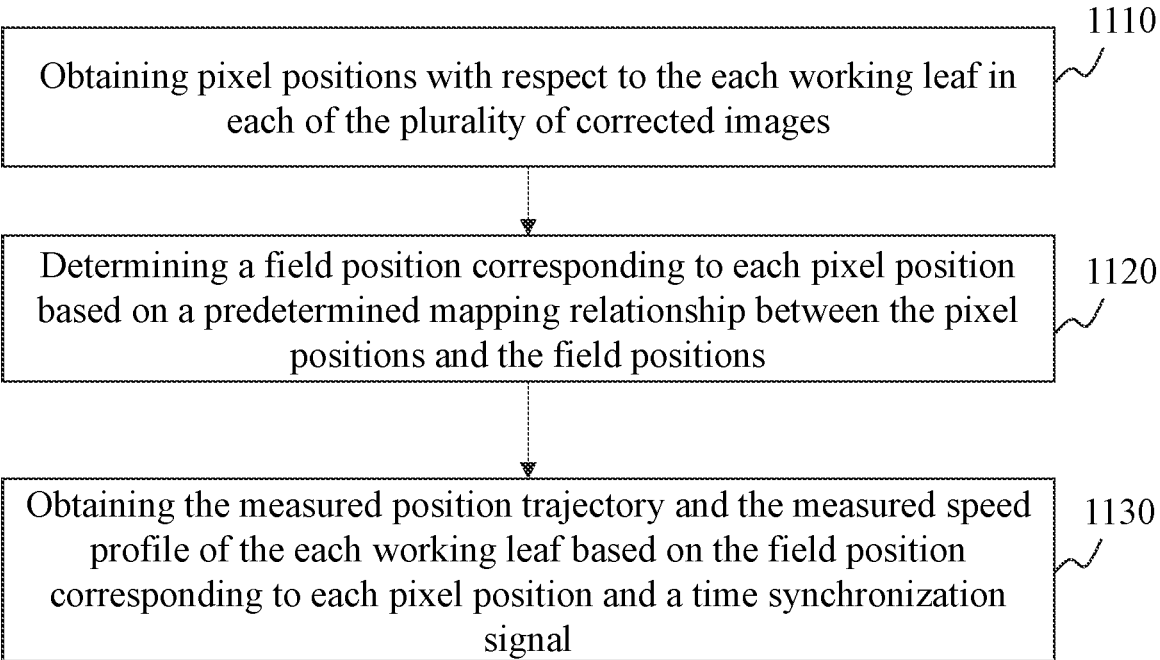
FIG. 11 is a flowchart illustrating an exemplary process for obtaining a measured position trajectory and a measured speed profile according to some embodiments of the present disclosure.

FIG. 11 is a flowchart illustrating an exemplary process 1100 for obtaining a measured position trajectory and a measured speed profile according to some embodiments of the present disclosure. In some embodiments, process 1100 may be executed by the RT system 100. For example, the process 1100 may be implemented as a set of instructions (e.g., an application) stored in a storage device (e.g., the storage device 150, the storage device 220, and/or the storage 390). In some embodiments, the processing device 140 (e.g., the processor 210 of the computing device 200, the CPU 340 of the mobile device 300, and/or one or more modules illustrated in FIG. 4) may execute the set of instructions and may accordingly be directed to perform the process 1100.

In some embodiments, the process 1100 may be performed for each working leaf of a plurality of working leaves. In 1110, the processing device 140 (e.g., the trajectory error determining module 450) may obtain pixel positions with respect to the each working leaf in each of the plurality of corrected images.

In some embodiments, each working leaf may be represented on a corrected image as a plurality of pixels. For example, the processing device 140 may identify the plurality of pixels according to an edge gradient algorithm or a 50% gray value point algorithm. The processing device 140 may identify the pixel positions of the plurality of pixels in each corrected image.

In 1120, the processing device 140 (e.g., the trajectory error determining module 450) may determine a field position corresponding to each pixel position based on a predetermined mapping relationship between the pixel positions and the field positions.

In some embodiments, the predetermined mapping relationship may include a plurality mapping pairs. A mapping pair may include a pixel position and a corresponding field position. The predetermined mapping relationship may be predetermined and stored in a storage device (e.g., the storage device 150, the storage device 220, and/or the storage 390). The processing device 140 may look up the predetermined mapping relationship using each pixel position to obtain the corresponding field position.

In 1130, the processing device 140 (e.g., the trajectory error determining module 450) may obtain the measured position trajectory and the measured speed profile of the each working leaf based on the field position corresponding to each pixel position and a time synchronization signal.

In some embodiments, the time synchronization signal may be configured to synchronize a first measured time of the measured position trajectory with a first planned time of the planned position trajectory. In some embodiments, the time synchronization signal may be configured to synchronize a second measured time of the measured speed profile with a second planned time of the planned speed profile. The processing device 140 may determine a trajectory of measured positions with time as the measured position trajectory based on the field position corresponding to the each pixel position. The processing device 140 may determine a trajectory of measured speeds with time as the measured speed profile based on the field position corresponding to the each pixel position. In some embodiments, the processing device 140 may determine a trajectory of measured positions with radiation dose and/or with rotation angles as the measured position trajectory. The measured position trajectory with radiation dose and/or with rotation angles may be compared with the corresponding planned position trajectory with radiation dose and/or with rotation angles to evaluate the dynamic errors of the plurality of working leaves at each control point.

It should be noted that the above description regarding the process 1100 is merely provided for the purposes of illustration, and not intended to limit the scope of the present disclosure. For persons having ordinary skills in the art, multiple variations and modifications may be made under the teachings of the present disclosure. In some embodiments, the process 1100 may be accomplished with one or more additional operations not described and/or without one or more of the operations discussed above. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claimed subject matter may lie in less than all features of a single foregoing disclosed embodiment.

What is claimed is:

1. A system for dynamic multileaf collimator (MLC) tracking, comprising:

at least one storage device including a set of instructions for dynamic MLC tracking; and at least one processor in communication with the at least one storage device, wherein when executing the set of instructions, the at least one processor is directed to cause the system to perform operations including:

identifying a plurality of working leaves of the MLC at a control point;

determining, for the control point, a signal acquisition region of an electronic portal imaging device (EPID) based on a plurality of planned position trajectories of the plurality of working leaves, wherein the signal acquisition region is part of an imaging plane of the EPID and includes a plurality of acquisition rows, and one or more detectors of the EPID acquire signals from the signal acquisition region; and obtaining an image from the EPID at the control point, wherein the image includes information acquired in the signal acquisition region.

2. The system of claim 1, the operations further including: determining a sampling rate of the EPID at the control point based on a planned speed profile of each of the plurality of working leaves, wherein the image is captured by the EPID using the sampling rate at the control point.

3. The system of claim 1, wherein the determining, for the control point, the signal acquisition region of the EPID includes:

obtaining leaf information of the plurality of working leaves based on the plurality of planned position trajectories of the plurality of working leaves; and determining a start acquisition row and an end acquisition row of the plurality of acquisition rows based on the leaf information of the plurality of working leaves and EPID information of the EPID.

4. The system of claim 3, wherein the leaf information of the plurality of working leaves includes information of a start working leaf, information of an end working leaf, position information of a center leaf of the MLC, and a projection width of a leaf projected upon an isocenter plane of the MLC.

5. The system of claim 3, wherein the EPID information of the EPID includes a pixel size of the EPID, an image size of an image captured by the EPID, a source image distance (SID), and an offset value of a center of the EPID with respect to a beam central axis at the control point.

6. The system of claim 2, wherein the determining a sampling rate of the EPID at the control point includes:

obtaining a maximum leaf speed of a leaf among all leaves of the MLC;

obtaining a maximum sampling rate of the EPID;

obtaining, among the plurality of working leaves, a maximum working leaf speed of a working leaf at the control point based on a planned speed profile of each of the plurality of working leaves; and determining the sampling rate of the EPID at the control point based on the maximum leaf speed, the maximum sampling rate of the EPID, and the maximum working leaf speed at the control point.

7. The system of claim 1, wherein the plurality of planned position trajectories of the plurality of working leaves are determined based on a treatment plan.

8. The system of claim 2, wherein the planned speed profile of each of the plurality of working leaves is determined based on a treatment plan.

9. The system of claim 2, the operations further including:

obtaining a plurality of images each of which corresponds to data acquired by the EPID in the signal acquisition region using the sampling rate at one of a plurality of control points; and for each of the plurality of working leaves, determining a measured position trajectory and a measured speed profile of the each working leaf based on the plurality of images;

determining a position trajectory error of the each working leaf based on the planned position trajectory and the measured position trajectory of the each working leaf; and determining a speed profile error of the each working leaf based on the planned speed profile and the measured speed profile of the each working leaf.

10. The system of claim 9, wherein the determining a measured position trajectory and a measured speed profile of each of the plurality of working leaves based on the plurality of images includes:

obtaining a plurality of corrected images by correcting, based on an image correction algorithm, the plurality of images; and determining the measured position trajectory and the measured speed profile of the each working leaf based on the plurality of corrected images.

11. The system of claim 10, wherein the determining the measured position trajectory and the measured speed profile of the each working leaf based on the plurality of corrected images includes:

for each of the plurality of working leaves, obtaining pixel positions with respect to the each working leaf in each of the plurality of corrected images;

determining a field position corresponding to each pixel position based on a predetermined mapping relationship between the pixel positions and the field positions; and obtaining the measured position trajectory and the measured speed profile of the each working leaf based on the field position corresponding to each pixel position and a time synchronization signal, wherein the time synchronization signal is configured to synchronize a first measured time of the measured position trajectory with a first planned time of the planned position trajectory, and synchronize a second measured time of the measured speed profile with a second planned time of the planned speed profile.

12. A method for dynamic multileaf collimator (MLC) tracking, implemented on a computing device having at least one processor and at least one computer-readable storage medium, the method comprising:

identifying a plurality of working leaves of the MLC at a control point;

determining, for the control point, a signal acquisition region of an electronic portal imaging device (EPID) based on a plurality of planned position trajectories of the plurality of working leaves, wherein the signal acquisition region is part of an imaging plane of the EPID and includes a plurality of acquisition rows, and one or more detectors of the EPID acquire signals from the signal acquisition region; and obtaining an image from the EPID at the control point, wherein the image includes information acquired in the signal acquisition region.

13. The method of claim 12, further comprising:

determining a sampling rate of the EPID at the control point based on a planned speed profile of each of the plurality of working leaves, wherein the image is captured by the EPID using the sampling rate at the control point.

14. The method of claim 12, wherein the determining, for the control point, the signal acquisition region of the EPID includes:

obtaining leaf information of the plurality of working leaves based on the plurality of planned position trajectories of the plurality of working leaves; and determining a start acquisition row and an end acquisition row of the plurality of acquisition rows based on the leaf information of the plurality of working leaves and EPID information of the EPID.

15. The method of claim 14, wherein the leaf information of the plurality of working leaves includes information of a start working leaf, information of an end working leaf, position information of a center leaf of the MLC, and a projection width of a leaf projected upon an isocenter plane of the MLC.

16. The method of claim 14, wherein the EPID information of the EPID includes a pixel size of the EPID, an image size of an image captured by the EPID, a source image distance (SID), and an offset value of a center of the EPID with respect to a beam central axis at the control point.

17. The method of claim 13, wherein the determining a sampling rate of the EPID at the control point includes:

obtaining a maximum leaf speed of a leaf among all leaves of the MLC;

obtaining a maximum sampling rate of the EPID;

obtaining, among the plurality of working leaves, a maximum working leaf speed of a working leaf at the control point based on a planned speed profile of each of the plurality of working leaves; and determining the sampling rate of the EPID at the control point based on the maximum leaf speed, the maximum sampling rate of the EPID, and the maximum working leaf speed at the control point.

18. The method of claim 12, wherein the plurality of planned position trajectories of the plurality of working leaves are determined based on a treatment plan.

19. The method of claim 13, wherein the plurality of planned speed profiles of the plurality of working leaves are determined based on a treatment plan.

20. A non-transitory readable medium, comprising at least one set of instructions for dynamic multileaf collimator (MLC) tracking, wherein when executed by at least one processor of an electrical device, the at least one set of instructions directs the at least one processor to perform a method, the method comprising:

identifying a plurality of working leaves of the MLC at a control point;

determining, for the control point, a signal acquisition region of an electronic portal imaging device (EPID) based on a plurality of planned position trajectories of the plurality of working leaves, wherein the signal acquisition region is part of an imaging plane of the EPID and includes a plurality of acquisition rows, and one or more detectors of the EPID acquire signals from the signal acquisition region; and obtaining an image from the EPID at the control point, wherein the image includes information acquired in the signal acquisition region.

* * * * *